US010036732B2

(12) United States Patent
Yoon et al.

(10) Patent No.: US 10,036,732 B2
(45) Date of Patent: Jul. 31, 2018

(54) ULTRASONIC INSPECTION DEVICE FOR SMALL BORE PIPES

(71) Applicant: KOREA HYDRO & NUCLEAR POWER CO., LTD, Gyeongju-si (KR)

(72) Inventors: Byoung Sik Yoon, Daejeon (KR); Yong Sik Kim, Daejeon (KR); Jeong Seok Lee, Daejeon (KR); Tae Hun Lee, Daejeon (KR)

(73) Assignee: Korea Hydro & Nuclear Power Co., Ltd., Gyeongju-si (KR)

( * ) Notice: Subject to any disclaimer, the term of this patent is extended or adjusted under 35 U.S.C. 154(b) by 79 days.

(21) Appl. No.: 15/033,065

(22) PCT Filed: Aug. 19, 2014

(86) PCT No.: PCT/KR2014/007644
§ 371 (c)(1),
(2) Date: Apr. 28, 2016

(87) PCT Pub. No.: WO2015/064901
PCT Pub. Date: May 7, 2015

(65) Prior Publication Data
US 2016/0252482 A1   Sep. 1, 2016

(30) Foreign Application Priority Data

Oct. 30, 2013 (KR) ........................ 10-2013-0130020

(51) Int. Cl.
*G01N 29/04*   (2006.01)
*G01N 29/265*   (2006.01)
*G01N 29/22*   (2006.01)

(52) U.S. Cl.
CPC ......... *G01N 29/041* (2013.01); *G01N 29/043* (2013.01); *G01N 29/223* (2013.01);
(Continued)

(58) Field of Classification Search
CPC .. G01N 29/041; G01N 29/225; G01N 29/043; G01N 29/223; G01N 29/265;
(Continued)

(56) References Cited

U.S. PATENT DOCUMENTS 2,908,161 A * 10/1959 Bincer ................... G01N 29/26
310/336
2005/0258648 A1* 11/2005 Newman ................ F16L 23/10
285/364
2009/0314089 A1* 12/2009 Brignac ............... G01N 29/226
73/622

FOREIGN PATENT DOCUMENTS

JP    2004-294128 A    10/2004
JP    2013-174531 A     9/2013
(Continued)

OTHER PUBLICATIONS

PCT International Search Report for counterpart PCT Application No. PCT/KR2014/007644, 5 pp. (including English translation), (dated Dec. 16, 2014).
(Continued)

*Primary Examiner* — Paul West
*Assistant Examiner* — Xin Zhong
(74) *Attorney, Agent, or Firm* — Womble Bond Dickinson (US) LLP (57) ABSTRACT

The present invention relates to an ultrasonic inspection device for small bore pipes comprising: a first arc-shaped frame part and a second arc-shaped frame part which surround the circumference of a pipe when combined with the pipe, and which have one side thereof rotationally connected to each other by means of a rotary connecting pin; an adjustment part that connects the other side of the first arc-shaped frame part and the other side of the second arc-shaped frame part to each other and is capable of adjusting the diameter of the bore formed by the first arc-shaped frame part and the second arc-shaped frame part according to the diameter of the pipe; a probe fixing part for fixing a probe to the first arc-shaped frame part such that the probe comes into contact with the surface of the pipe; an encoder part which is provided to the second arc-shaped frame part and maintains an encoder at a predetermined
(Continued)

distance from the pipe; and a plurality of roller parts which are provided to the first arc-shaped frame part and the second arc-shaped frame part and rotate around the circumference of the pipe contacting the pipe in a state where the first arc-shaped frame part and the second arc-shaped frame part are connected to each other. The present invention includes two arc-shaped frame parts which surround the circumference of a pipe and is able to adjust the diameter of the bore of a ring-shaped frame part obtained according to connection of the two arc-shaped frame parts, and thus is applicable irrespective of the diameter of the pipe within a predetermined range, thereby improving work convenience and reducing costs.

2 Claims, 7 Drawing Sheets

(52) U.S. Cl.
CPC ......... *G01N 29/225* (2013.01); *G01N 29/265* (2013.01); *G01N 2291/0258* (2013.01); *G01N 2291/0289* (2013.01); *G01N 2291/044* (2013.01); *G01N 2291/267* (2013.01); *G01N 2291/2634* (2013.01)

(58) Field of Classification Search
CPC ..... G01N 2291/044; G01N 2291/0258; G01N 2291/267; G01N 2291/0289; G01N 2291/2634
See application file for complete search history.

(56) References Cited

FOREIGN PATENT DOCUMENTS

| | | |
|---|---|---|
| KR | 10-2008-0024570 A | 3/2008 |
| KR | 10-2010-0039702 A | 4/2010 |
| KR | 10-1103801 B1 | 1/2012 |
| KR | 10-2013-0029888 A | 3/2013 |

OTHER PUBLICATIONS

PCT Written Opinion of the International Searching Authority for counterpart PCT Application No. PCT/KR2014/007644, 5 pp., (dated Dec. 16, 2014).

\* cited by examiner

ULTRASONIC INSPECTION DEVICE FOR SMALL BORE PIPES

CROSS-REFERENCE TO RELATED APPLICATIONS

This patent application is a U.S. National Phase Application under 35 U.S.C. § 371 of International Application No. PCT/KR2014/007644, filed Aug. 19, 2014, entitled ULTRASONIC INSPECTION DEVICE FOR SMALL BORE PIPES, which claims priority to Korean Patent Application No. 10-2013-0130020, filed Oct. 30, 2013.

TECHNICAL FIELD

The present invention relates to an ultrasonic inspection device for small bore pipes, and in particular to an ultrasonic inspection device for small bore pipes which can be movable in an axial direction and can be rotatable in a circumferential direction, wherein a result of the inspection can be evaluated by a 3-dimensional method.

BACKGROUND ART

A nuclear power plant in general is configured to generate electric power in such way that a first cooling water is heated using the energy generated during a nuclear fission which is carried out using nuclear fuels in the inside of the nuclear power plant, and a steam turbine is rotated using the steam generated by a steam generator after the energy is transferred to a second cooling water with the aid of the energy of the heated first cooling water, and the rotational kinetic energy of the steam turbine is converted into an electric energy by an electric power generator. Inside the nuclear power plant, a number of pipes with various sizes are connected so as to supply a first line steam heated inside a nuclear reactor and various cooling waters, and the pipes are connected by a welding method.

Among the aforementioned various size pipes installed inside the nuclear power plant, small bore pipes are installed, the diameters of which are smaller than or equal to 50 mm. A socket may be connected between the pipes so as to change the directions of the small bore pipes, and the pipe and the socket are connected by the welding method.

The welded portions of the small bore pipes may continuously receive fatigue-associated damages due to the mechanical vibrations which are transferred from various devices during the operation of the nuclear power plant. For this reason, errors may frequently occur. In order to prevent the aforementioned errors, it needs to check any defects at the welded portions of the socket with the aid of an ultrasonic inspection method during the operation of the nuclear power plant.

The ultrasonic inspection method currently used for the small bore pipes inside the atom power plant in general is carried out in such a way that an inspector supplies an ultrasonic wave toward the welded portions of the socket from the side of the pipe or a coupler by using an ultrasonic probe, and an ultrasonic wave which has reflected off any defect portion is received, thus evaluating a defect state based on the signals which have shown at an ultrasonic inspection meter.

According to the aforementioned manual inspection method, an inspector should check the signals while moving with the user's hand holding the ultrasonic probe, whereupon it is difficult to maintain the contacts constant between the probe and the pipe, and the signals at the screen of the ultrasonic inspection meter should be analyzed while simultaneously checking the contact state between the ultrasonic probe and the pipe. In this case, the inspector cannot focus on the signal evaluation work, so the defect-associated signals may be missed.

A scanner has been newly developed so as to improve the aforementioned problems, wherein the scanner can be rotated while maintaining a predetermined constant contact state between the ultrasonic probe and the pipe.

The Korean patent registration number 10-1103801 (a scanner for inspecting the volume of a narrow space fillet welding portion which was registered on Jan. 2, 2012) describes a scanner which is able to detect any defect at a pipe welding portion in a narrow space.

The scanner described in the Korean patent registration number 10-1103801 is coupled to a pipe using an upper case and a lower case, and a plurality of driving wheels are provided at the insides of the upper case and the lower case. The scanner can rotate in the circumferential direction of the pipe in a state where the upper case and the lower case are coupled to each other.

The welded portions can be inspected while moving in the longitudinal direction of the pipe the probe fixed at a probe holder which is provided at an end portion of the index the length of which can be adjusted per unit (refer to the paragraph number [0035] of the Korean patent registration number 10-1103801) of one step at the top of the upper case.

In case of the aforementioned Korean patent registration number 10-1103801, an insertion groove into which the pipe is inserted is formed at a contact portion between the upper case and the lower case, and the driving wheels are disposed with an angle of 120° between them in such a way that the rotation center can position at the same distance with respect to the center of the insertion groove, which makes it possible to respond to any change in the diameter of the pipe.

More specifically, the small bore pipes have the diameters between 10 and 50 mm. In case of the aforementioned registered patent, since it is impossible to flexibly respond to any difference in the diameter of the pipe, the upper case and the lower case should be additionally manufactured and supplied, which are able to respond to the sizes of each pipe.

When it needs to inspect the pipes with various diameters, the inspector should carry a plurality of scanners which can be coupled to the pipes with different diameters, thus causing inconveniences, and the manufacturing thereof costs a lot.

SUMMARY

Accordingly, the present invention is made in an effort to resolve the above-mentioned problems. It is an object of the present invention to provide an ultrasonic inspection device for small bore pipes which can be employed irrespective of the diameters of the pipes.

It is another object of the present invention to provide an ultrasonic inspection device for small bore pipes which is able to maintain a constant contact pressure between a probe and an encoder.

To achieve the above objects, there is provided an ultrasonic inspection device for small bore pipes, which may include, but is not limited to, a first arc-shaped frame part and a second arc-shaped frame part which are disposed covering the surrounding of a pipe when they are combined with the pipe, and one side of each of the first arc-shaped frame part and the second arc-shaped frame part are coupled rotatable to each other with the aid of a rotary connecting pin; an adjustment part which is able to couple the other side of each of the first arc-shaped frame part and the second arc-shaped frame part and is provided to adjust the size of the inner diameter defined by the first arc-shaped frame part and the second arc-shaped frame part in response to the diameter of the pipe; a probe fixing part which is provided to allow the probe to contact with the surface of the pipe in such a way to fix the probe at the first arc-shaped frame part; an encoder part which is provided at the second arc-shaped frame part so as to maintain the encoder at a predetermined distance from the pipe; and a plurality of roller parts which are provided at the first arc-shaped frame part and the second arc-shaped frame part and are able to rotate, contacting with the pipe, along the surrounding of the pipe in a state where the first arc-shaped frame part and the second arc-shaped frame part are combined with each other.

The ultrasonic inspection device for small bore pipes according to the present invention is equipped with two arc-shaped frame parts formed covering the surrounding of a pipe. Since the inner diameter of a circular frame part to which the two arc-shaped frame parts are coupled can be adjusted, the ultrasonic inspection device for small bore pipes according to the present invention can be employed within a predetermined diameter range irrespective of the diameters of the pipes, whereupon work convenience can be enhanced, and the manufacturing cost can be saved.

In addition, the ultrasonic inspection device for small bore pipes according to the present invention is able to prevent the occurrence of any detection errors due to the difference in a contact pressure between the probe contacting with the pipe and the encoder since the aforementioned contact pressure can be maintained constant.

DETAILED DESCRIPTION

The ultrasonic inspection device for small bore pipes according to the present invention, which may include, but is not limited to, a first arc-shaped frame part and a second arc-shaped frame part which are disposed covering the surrounding of a pipe when they are combined with the pipe, and one side of each of the first arc-shaped frame part and the second arc-shaped frame part are coupled rotatable to each other with the aid of a rotary connecting pin; an adjustment part which is able to couple the other side of each of the first arc-shaped frame part and the second arc-shaped frame part and is provided to adjust the size of the inner diameter defined by the first arc-shaped frame part and the second arc-shaped frame part in response to the diameter of the pipe; a probe fixing part which is provided to allow the probe to contact with the surface of the pipe in such a way to fix the probe at the first arc-shaped frame part; an encoder part which is provided at the second arc-shaped frame part so as to maintain the encoder at a predetermined distance from the pipe; and a plurality of roller parts which are provided at the first arc-shaped frame part and the second arc-shaped frame part and are able to rotate, contacting with the pipe, along the surrounding of the pipe in a state where the first arc-shaped frame part and the second arc-shaped frame part are connected to each other.

The configuration and operation of the ultrasonic inspection device for small bore pipes according to the present invention will be described with reference to the accompanying drawings.

Figure 1:
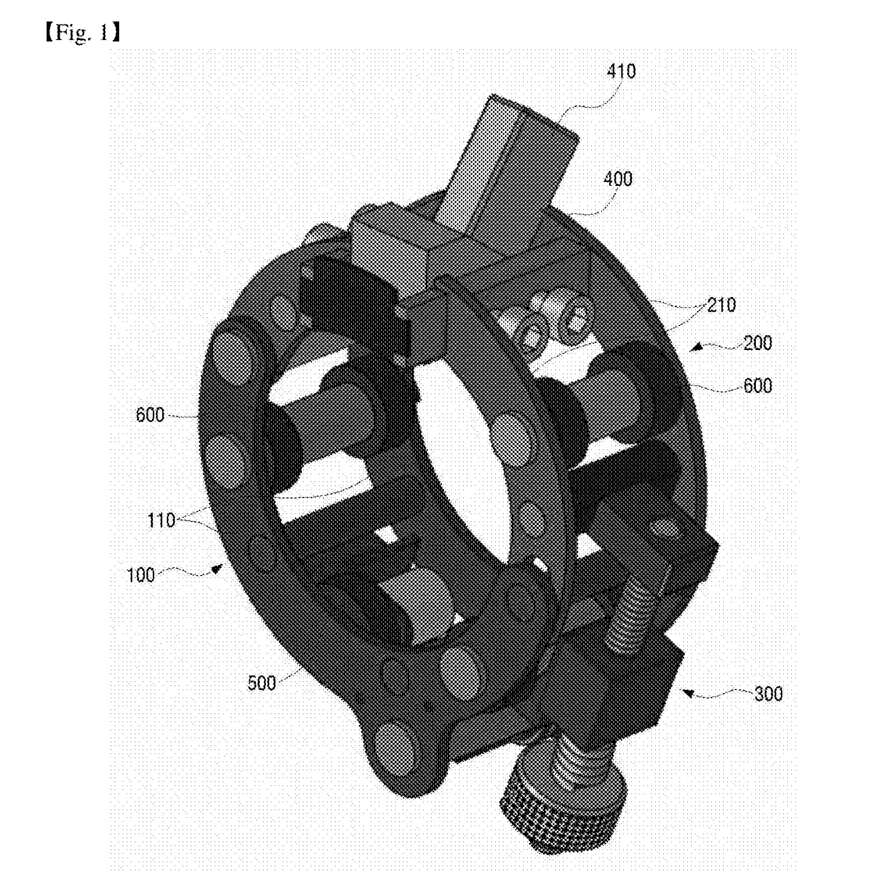
FIG. 1 is a perspective view illustrating an engaged state of an ultrasonic inspection device for small bore pipes according to a preferred embodiment of the present invention.
Figure 2:
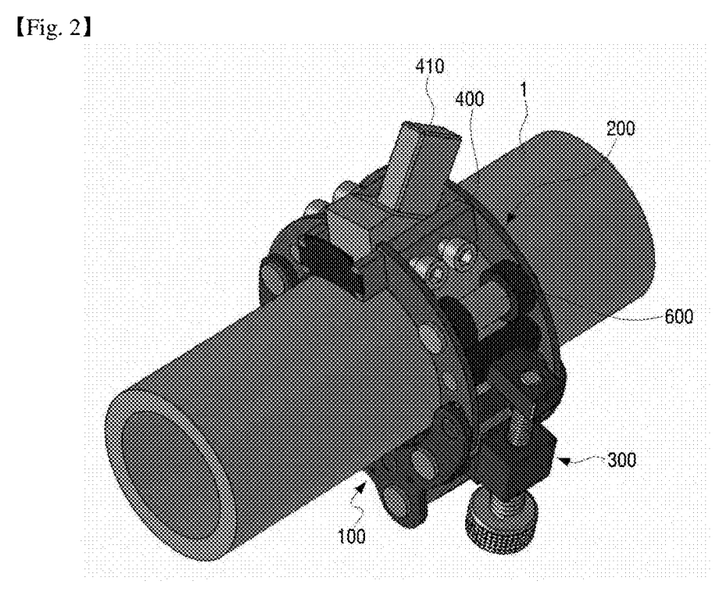
FIG. 2 is a perspective view illustrating an engaged state of a pipe in FIG. 1.
Figure 3:
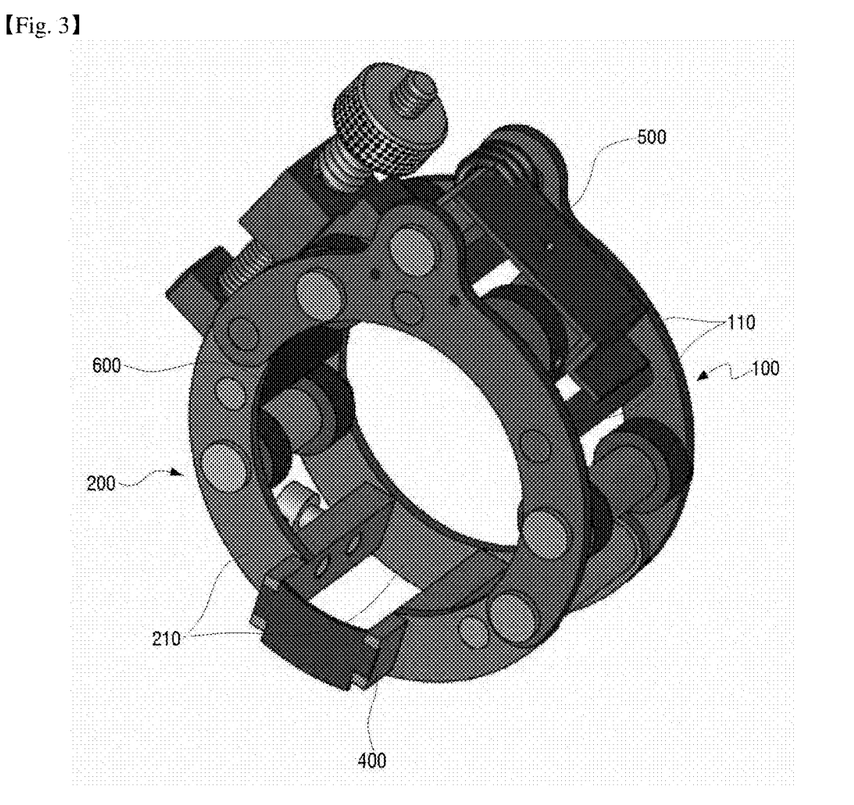
FIG. 3 is a perspective view illustrating an engaged state of an ultrasonic inspection device for small bore pipes from which a probe is removed according to a preferred embodiment of the present invention.
Figure 4:
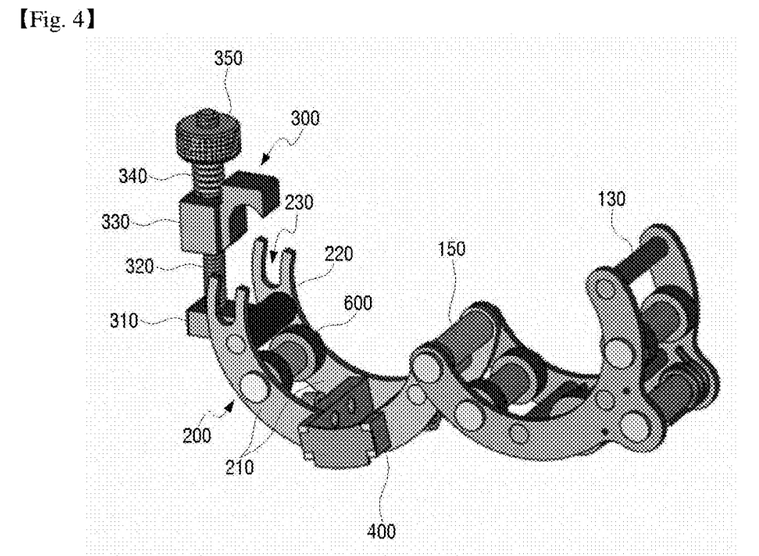
FIG. 4 is a perspective view illustrating a separated state in FIG. 3.

FIG. 1 is a perspective view illustrating an engaged state of an ultrasonic inspection device for small bore pipes according to a preferred embodiment of the present invention. FIG. 2 is a perspective view illustrating an engaged state of a pipe in FIG. 1. FIG. 3 is a perspective view illustrating an engaged state of an ultrasonic inspection device for small bore pipes from which a probe is removed according to a preferred embodiment of the present invention. FIG. 4 is a perspective view illustrating a separated state in FIG. 3.

Referring to FIG. 1, the ultrasonic inspection device for small bore pipes according to an embodiment of the present invention may include, but is not limited to, a first arc-shaped frame part 100 and a second arc-shaped frame part 200 which are connected via an inter-rotary connecting pin 150 and are disposed covering the surrounds of a pipe 1, an adjustment part 300 which is able to fixedly couple the opposite ends of the first arc-shaped frame part 100 and the second arc-shaped frame part 200 and is provided to adjust the diameter defined by the first arc-shaped frame part 100 and the second arc-shaped frame part 200 in response to the diameter of the pipe 1 and adjust the pressure that the first arc-shaped frame 100 and the second arc-shaped frame 200 are contacted close with the pipe 1, an encoder part 500 which is provided at the first arc-shaped frame part 100, a probe fixing part 400 which is provided at the second arc-shaped frame part 200 so as to contact the probe 410 with the surface of the pipe 1, and a plurality of roller parts 600 which are provided at the first arc-shaped part 100 and the second arc-shaped part 200 and are able to allow the first arc-shaped frame part 100 and the second arc-shaped frame part 200, which are combined with each other while contacting with the surface of the pipe 1, to rotate along the surrounding of the pipe 1.

The configuration and operations of the ultrasonic inspection device for small bore pipes according to an embodiment of the present invention will be described in details.

The first arc-shaped frame part 100 and the second arc-shaped frame part 200 include two opposite arc-shaped frames 110 and 210, and a plurality of fixing pins 120 and 220 provided to interconnect the two arc-shaped frames 110 and 210.

One end of each of the two arc-shaped frames 110 of the first arc-shaped frame part 100 and one end of each of the two arc-shaped frames 210 of the second arc-shaped frame part 200 are interconnected via the rotary connecting pin 150 and are configured rotatable about the rotary connecting pin 150.

The pipe 1 will be inserted into the inside of the coupling structure of the first arc-shaped frame part 100 and the second arc-shaped frame part 200 in a state where the intermediate portion between the first arc-shaped frame part 100 and the second arc-shaped frame part 200 is widened, and the intermediate portion between the first arc-shaped frame part 100 and the second arc-shaped frame part 200 can be adjusted to cover an outer surrounding of the pipe 1.

A coupling fixing pin 130 is provided at the other end of each of the two arc-shaped frames 110 of the second arc-shaped frame part 100. The coupling fixing pin 130 actually has the same configuration as another fixing pin 120, provided that, as a different feature, the coupling fixing pin 130 is inserted into the other end of each of the two arc-shaped frames 210 of the second arc-shaped frame part 200.

An arc-shaped cut-away groove 230 into which the coupling fixing pin 130 is inserted, is formed at the other end of each of the two arc-shaped frames 210 of the second arc-shaped frame part 200, and the length of the cut-away groove 230 is larger than the diameter of the coupling fixing pin 130, by means of which the position of the coupling fixing pin 130 can be variable.

This configuration means that the inner diameter can change in response to the diameter of the pipe 1 when the first arc-shaped frame part 100 and the second arc-shaped frame part 200 according to the present invention are interconnected to each other, whereupon the present invention can be employed irrespective of the size of the small bore pipe 1.

A fixing pin 220 may be provided at an inner portion of the cut-away groove 230 of the second arc-shaped frame 200 so as to interconnect the two arc-shaped frames 210. An adjustment part 300 is fixed at the fixing pin 220.

Figure 5:
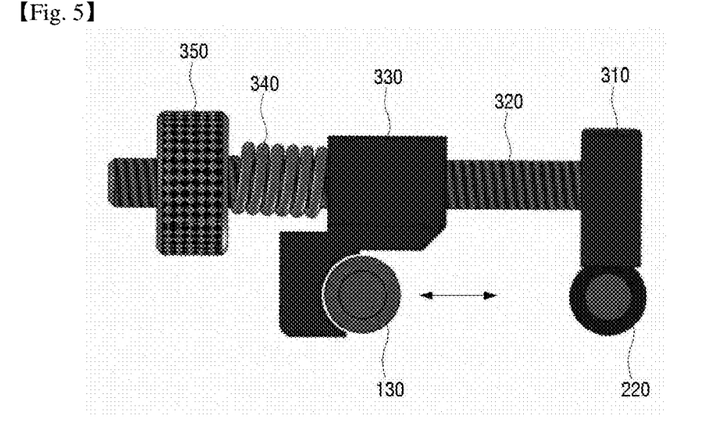
FIG. 5 is a view illustrating a detailed configuration of a pipe diameter adjustment part according to the present invention.

FIG. 5 is a detailed view illustrating the adjustment part 300. The adjustment part 300 may include, but is not limited to, a fixed block 310 which is fixedly installed at the fixing pin 220 at the side of the cut-away groove 230 of the second arc-shaped frame part 240, a movable block 330 which is movable along a screw 320 combined with the fixed block 310 and is able to adjust the position of the coupling fixing pin 130 in the cut-away groove 230, a spring 340 into which the screw 320 is inserted and which is able to transfer an elastic force to the movable block 330 while contacting with the opposite surface of the surface which is facing the fixed block 310 of the movable block 330, and a knob 350 into which the screw 320 is inserted contacting with the other end of the spring 340 and which is configured to move the movable block 330 in such a way to transfer force to the movable block 330 via the spring 340 based on the rotation thereof.

The adjustment part 300 is able to interconnect the first arc-shaped frame part 100 and the second arc-shaped frame part 200 and maintain the coupled state thereof.

That is, in a state where the first arc-shaped frame part 100 and the second arc-shaped frame part 200 are disposed covering the outer surface of the pipe 1, the coupling fixing pin 130 of the first arc-shaped frame part 100 is inserted in the cut-away groove 230 of the second arc-shaped frame part 200. In this state, the movable block 330 is moved toward the fixed block 310 by adjusting the knob 350, and the coupling fixing pin 130 is not separated with the aid of the movable block 330, and the coupled state of the first arc-shaped frame part 100 and the second arc-shaped frame part 200 can be maintained stable.

Moreover, a recovery force of the spring 340 is continuously transferred to the movable block 330. This force is transferred to the coupling fixing pin 130. The probe 410 fixed by the probe fixing part 400 at a part of the first arc-shaped frame part 100 is able to maintain a constant contacting force when contacting with the pipe 1.

In this state, the first arc-shaped frame part 100 and the second arc-shaped frame part 200 are not directly contacting with the pipe 1. A part of a roller part 600 coupled rotatable to the first arc-shaped frame part 100 and the second arc-shaped frame part 200, instead, is contacting with the surface of the pipe 1. For this reason, the assembled body of the first arc-shaped frame part 100 and the second arc-shaped frame part 200 is rotatable along the surrounding of the pipe 1.

When the first arc-shaped frame part 100 and the second arc-shaped frame part 200 are rotated along the surrounding of the pipe 1, the probe 410 provided at the first arc-shaped frame part 100 will rotate along the surrounding of the pipe 1 in a state where the probe 410 is contacting with the pipe 1 with the aid of the probe fixing part 400, thus easily carrying out an inspection with respect to the welded portions of the pipe 1.

As aforementioned, the probe 410 is able to maintain a constant contact force with the aid of the spring 340, by means of which it is possible to prevent the occurrence of any errors during the inspection which may occur due to any difference in the contacting state.

The signals from the probe 410 will be received by the encoder of the encoder part 500 and will be transferred to the outside.

Figure 6:
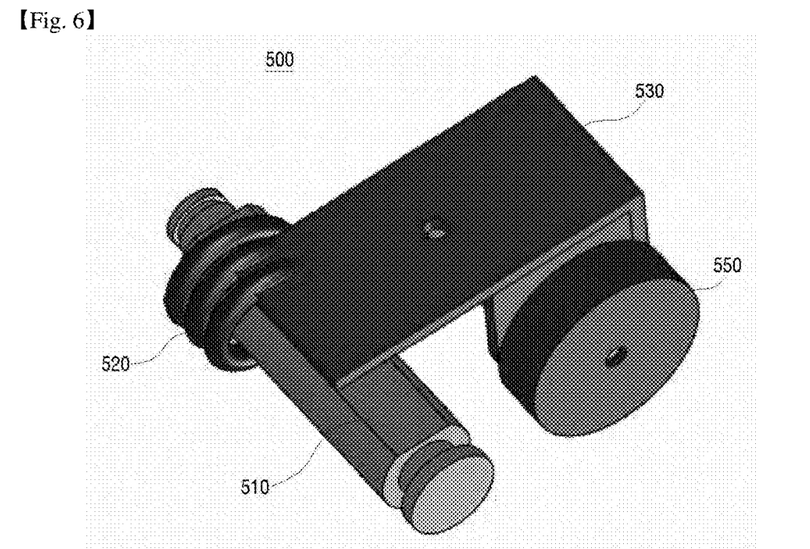
FIG. 6 is a view illustrating a detailed configuration of an encoder part according to the present invention.
Figure 7:
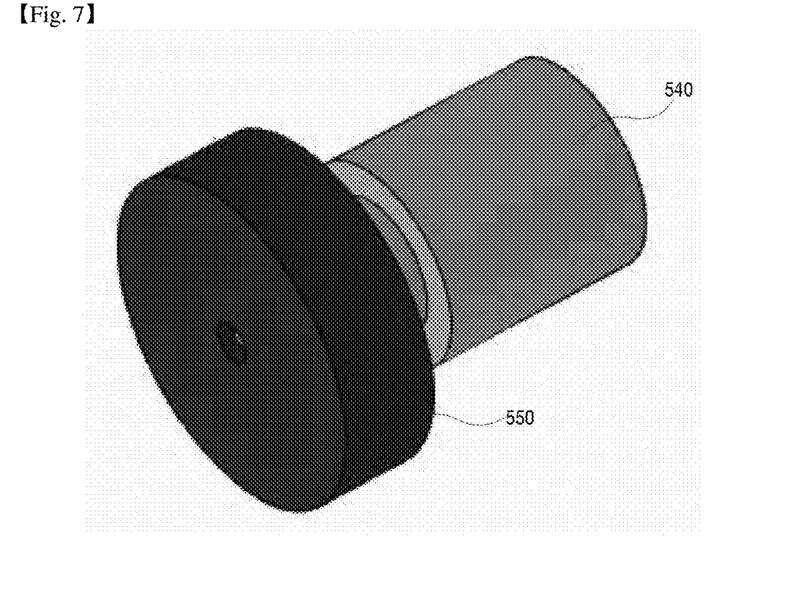
FIG. 7 is a perspective view illustrating an encoder and a roller in FIG. 6.

FIG. 6 is a view illustrating a configuration of the encoder part 500, and FIG. 7 is a view illustrating a partial configuration of the encoder part 500.

Referring to FIGS. 6, 7 and 1, the encoder part 500 according to the present invention may include, but is not limited to, a rotation pin 510 which is coupled rotatable to a protrusion part protruding outward from each of the two arc-shaped frames 210 of the second arc-shaped frame part 200, a pressing spring 520 into which the rotation pin 510 is inserted and which is able to provide an elastic force in the direction of 90° with respect to the axial direction of the rotation pin 510, an installation part 530 which is provided to receive a pressure in the direction of the surface of the pipe 1 with the aid of the pressing spring 520, an encoder 540 which is fixed at a lower portion of the installation part 530, and a wheel 550 which is coupled rotatable to an end portion of the encoder 540 and is disposed contacting with the surface of the pipe 1 and is configured to easily move along the surface surrounding of the pipe 1.

The diameter of the wheel 550 is larger than the diameter of the cylindrical encoder 540.

In this configuration, the installation part 530 provided to fix the encoder 540 may receive a pressure that the installation part 530 is pressed in the direction of the surface of the pipe 1 with the aid of the pressing spring 520. The encoder 540 is not actually contacting directly with the pipe 1, but the rotational radius can be maintained constant when rotating along the surrounding of the pipe 1.

For this reason, the signals of the probe 410 can be received always on the same conditions, which may allow to prevent any degradation in terms of the inspection reliability.

Figure 8:
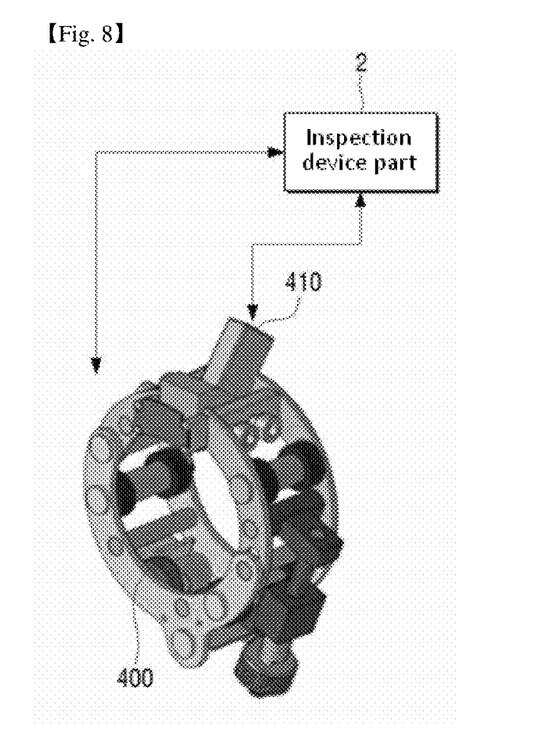
FIG. 8 is a view illustrating an ultrasonic inspection system for small bore pipes according to the present invention.

FIG. 8 is a view illustrating a configuration of the ultrasonic inspection system for small bore pipes according to an embodiment of the present invention.

Referring to FIG. 8, a cable is connected to the probe 410 and the encoder 540 of the ultrasonic inspection device for small bore pipes according to the present invention. This cable is connected to an ultrasonic inspection device part 2 and is able to transfer ultrasonic signals to the probe 410 and analyze the signals received via the encoder 540, thus detecting the position of any defect.

Figure 9:
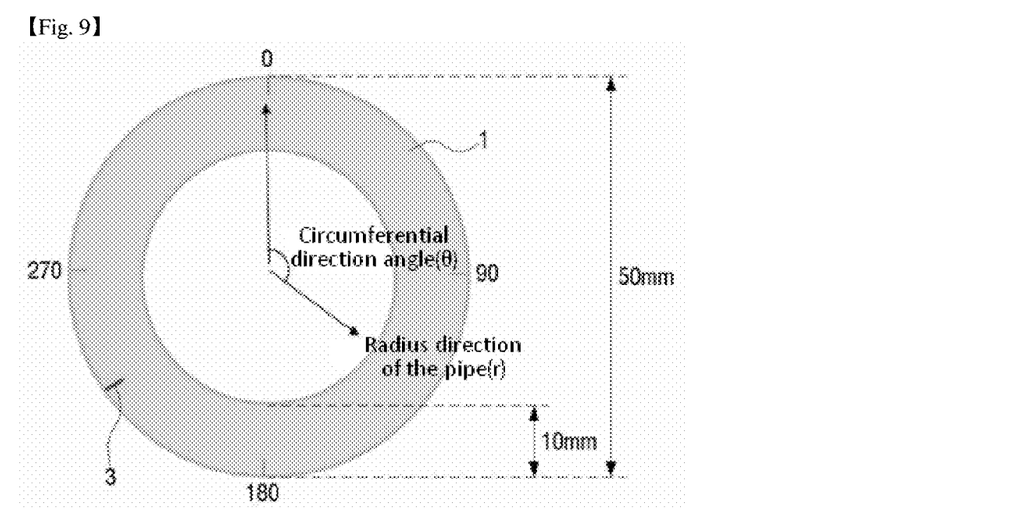
FIG. 9 is a cross sectional view illustrating a pipe which will be inspected according to the present invention.
Figure 10:
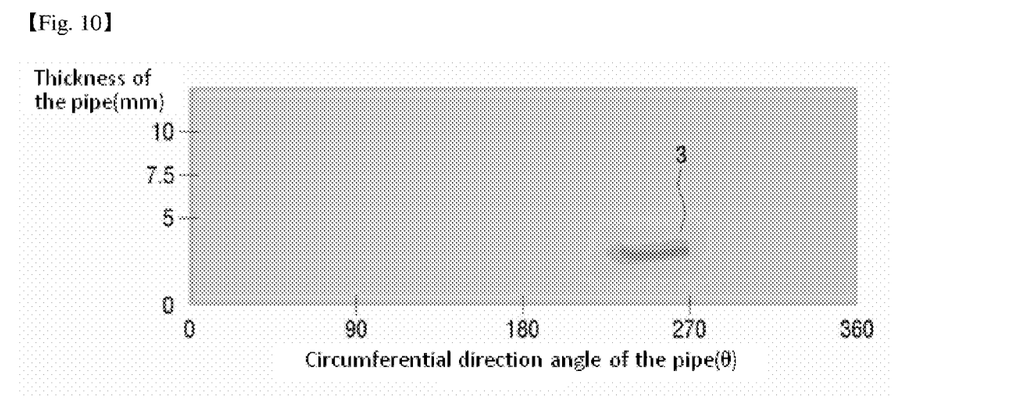
FIG. 10 is a graph showing a result of the inspection which has been carried out on a pipe in FIG. 9 according to the present invention.

FIGS. 9 and 10 is a cross sectional view illustrating a pipe which will be inspected according to the present invention, and FIG. 10 is a graph showing a result of the inspection which has been carried out using the ultrasonic inspection device for small bore pipes illustrated in FIG. 9 according to an embodiment of the present invention.

Referring to FIGS. 9 and 10, in case of the pipe 1, the circumferential direction angle (θ) in the clockwise direction with respect to the top of the pipe 1 can be determined, and the thickness of the radius direction (r) of the pipe 1 can be identified.

As illustrated in FIG. 9, a predetermined defect 3 may position between 180° and 270° which are the circumferential direction angles (θ), and the defect 3 may position within a distance of 5 mm from the surface.

The inspection may be carried out while rotating in the clockwise direction the portion illustrated in FIG. 9 along the surrounding of the pipe 1 with the aid of the ultrasonic inspection device for small bore pipes according to a preferred embodiment of the present invention.

The graph shown in FIG. 10 can be obtained after the aforementioned inspection, and it is possible to confirm the position of the defect 3 within a distance of 5 mm from the surface between 180° and 270° of the circumferential direction angle with the aid of the aforementioned graph.

The ultrasonic inspection can be carried out in such a way to rotate the device of the present invention along the surrounding of a predetermined portion of the pipe 1, thus detecting whether or not the defect 3 is present at the pipe 1. If the defect is detected, the position of the defect can be confirmed by a 3-dimensional method.

As the present invention may be embodied in several forms without departing from the spirit or essential characteristics thereof, it should also be understood that the above-described examples are not limited by any of the details of the foregoing description, unless otherwise specified, but rather should be construed broadly within its spirit and scope as defined in the appended claims, and therefore all changes and modifications that fall within the meets and bounds of the claims, or equivalences of such meets and bounds are therefore intended to be embraced by the appended claims.

What is claimed is:

1. An ultrasonic inspection device for small bore pipes, comprising:

a first arc-shaped frame part and a second arc-shaped frame part which surround the circumference of a pipe when combined with the pipe, and which have one side thereof rotationally connected to each other by means of a rotary connecting pin;

an adjustment part that connects the other side of the first arc-shaped frame part and the other side of the second arc-shaped frame part to each other and is capable of adjusting the diameter of the bore formed by the first arc-shaped frame part and the second arc-shaped frame part according to the diameter of the pipe;

a probe fixing part for fixing a probe to the first arc-shaped frame part such that the probe comes into contact with the surface of the pipe;

an encoder part which is provided at the second arc-shaped frame part so as to maintain the encoder at a predetermined distance from the pipe; and a plurality of roller parts which are provided to the first arc-shaped frame part and the second arc-shaped frame part and rotate around the circumference of the pipe contacting the pipe in a state where the first arc-shaped frame part and the second arc-shaped frame part are connected to each other, wherein the adjustment part comprises:

a fixed block fixed at a fixing pin at the side of a cut-away groove in the second arc-shaped frame part, a screw having a fixed end and a free end, the fixed end being fixed in the fixed block, a movable block movable along the screw and positioned between the fixed end of the screw and the free end of the screw, a knob engaged with the free end of the screw and positioned on the side of the movable block opposite the fixed block, and a spring having a first end and a second end, wherein the screw is inserted in the spring so that the first end of the spring is in contact with the movable block and the second end of the spring is in contact with the knob, wherein the spring transfers force from the knob to the movable block so that the knob can be used adjust the position of a coupling fixing pin in the cut-away groove;

wherein the encoder part comprises:

an encoder which is fixed at a lower portion of the installation part, and a wheel which is rotatably coupled to an end portion of the encoder and is disposed contacting with the surface of the pipe and is configured to move along the surface surrounding of the pipe.

2. The device of claim 1, wherein the cut-away groove into which the coupling fixing pin is inserted is formed at the other side of the second arc-shaped frame part, wherein the cut-away groove is formed longer than the diameter of the coupling fixing pin, and the adjustment part is provided to adjust, in the cut-away groove, the position of the coupling fixing pin.

\* \* \* \* \*